US00PP17226P3

(12) United States Plant Patent
Jensen

(10) Patent No.: US PP17,226 P3
(45) Date of Patent: Nov. 21, 2006

(54) ***CAMPANULA* PLANT NAMED 'PKMT01'**

(50) Latin Name: *Campanula tubulosa*
Varietal Denomination: PKMT01

(75) Inventor: Gert Kim Jensen, Odense (DK)

(73) Assignee: Gartneriet PKM ApS, Odense (DK)

( * ) Notice: Subject to any disclaimer, the term of this patent is extended or adjusted under 35 U.S.C. 154(b) by 0 days.

(21) Appl. No.: 11/059,409

(22) Filed: Feb. 17, 2005

(65) Prior Publication Data

US 2006/0185045 P1 Aug. 17, 2006

(51) Int. Cl.
*A01H 5/00* (2006.01)

(52) U.S. Cl. ..... Plt./263
(58) Field of Classification Search ..... Plt./263
See application file for complete search history.

(56) References Cited

PUBLICATIONS

European Union Community Plant Variety Office (CPVO) 2004/2246 filed Nov. 16, 2004—documents include Feb. 28, 2006 print–out from CPVO website verifying application information (1 pg) and Proposal for Variety Denomination (1 pg), Application Papers (7 pgs) and Technical Questionnaire (5 pgs).
Canadian Plant Breeder's Rights 05/4917 filed May 30, 2005—documents include Feb. 28, 2006 print–out from Canadian Food Inspection Agency—Plant Breeders' Rights Office List of Varieties verifying application information (1 pg) and Filing Receipt dated Nov. 26, 2004 (2 pgs).

*Primary Examiner*—Anne Marie Grunberg
*Assistant Examiner*—Georgia Helmer
(74) *Attorney, Agent, or Firm*—Foley & Lardner LLP

(57) ABSTRACT

A new and distinct cultivar of *Campanula* plant named 'PKMT01', characterized by having compact, upright plant habit; dense and bushy plant form; vigorous growth habit and large upright violet flowers.

2 Drawing Sheets

Latin name of genus and species of the plant claimed: *Campanula tubulosa.*
Variety denomination: 'PKMT01'.

BACKGROUND OF THE INVENTION

The present invention relates to a new and distinct cultivar of *Campanula* plant, botanically known as *Campanula tubulosa Engl.*, commonly known as Bellflower, and hereinafter referred to by the name 'PKMT01'.

The new *Campanula*, 'PKMT01', is a product of a planned breeding program conducted by the inventor, Gert K. Jensen, in Søhus, Denmark. The objective of the breeding program is to develop a new *Campanula* variety with upright, compact plant habit with large violet upright flowers.

The new *Campanula* cultivar, 'PKMT01', originated from a selection found by the inventor in 2001 in Søhus, Denmark, in a comparison batch of *Campanula tubulosa Engl.* plants (unpatented). The inventor selected the new *Campanula* cultivar on the basis of its compact and freely flowering habit. Plants of the new *Campanula* cultivar are more upright and compact and more freely flowering than plants of original species.

Asexual reproduction of the new *Campanula* cultivar by terminal cuttings taken and propagated since January of 2002 in Søhus, Denmark, has shown that the combination of characteristics as herein disclosed for the new cultivar are firmly fixed and retained through successive generations of asexual reproduction. The new cultivar reproduces true-to-type.

SUMMARY OF THE INVENTION

The following traits have been repeatedly observed and are determined to be the unique characteristics of 'PKMT01'. These characteristics in combination distinguish 'PKMT01' as a new and distinct cultivar:

1. Upright, compact plant habit.
2. Dense and bushy plant form, mainly due to short, unright stiff stems.
3. Vigorous growth habit, but no need for chemical growth retardation.
4. Larger quantity of flowers per plant.

Plants of the new cultivar, 'PKMT01' can be compared to wild plants of *Campanula tubulosa Engl.* In side-by-side comparisons conducted in Søhus Denmark, plants of 'PKMT01' differed from plants of the wild type in the following characteristics:

1. Plants of 'PKMT01' have larger violet, upright, single campanulate flowers than plants of the wild type.
2. Plants of 'PKMT01' have shorter internodes, petioles and leaves than plants of the wild type.
3. Plants of 'PKMT01' have more upright growth than plants of the wild type.
4. Plants of 'PKMT01' have shorter flower peduncles than plants of the wild type.
5. Plants of 'PKMT01' are shorter and more compact than plants of the wild type.
6. Plants of 'PKMT01' have more flowers per plant than plants of the wild type.

BRIEF DESCRIPTION OF THE DRAWINGS

The accompanying colored photographs illustrate the overall appearance of the new cultivar 'PKMT01', showing the colors as true as it is reasonably possible to obtain in colored reproductions of this type. Colors in the photographs may differ slightly from the color values cited in the detailed botanical description, which more accurately describe the actual colors of 'PKMT01'.

DETAILED BOTANICAL DESCRIPTION

Figure 1:
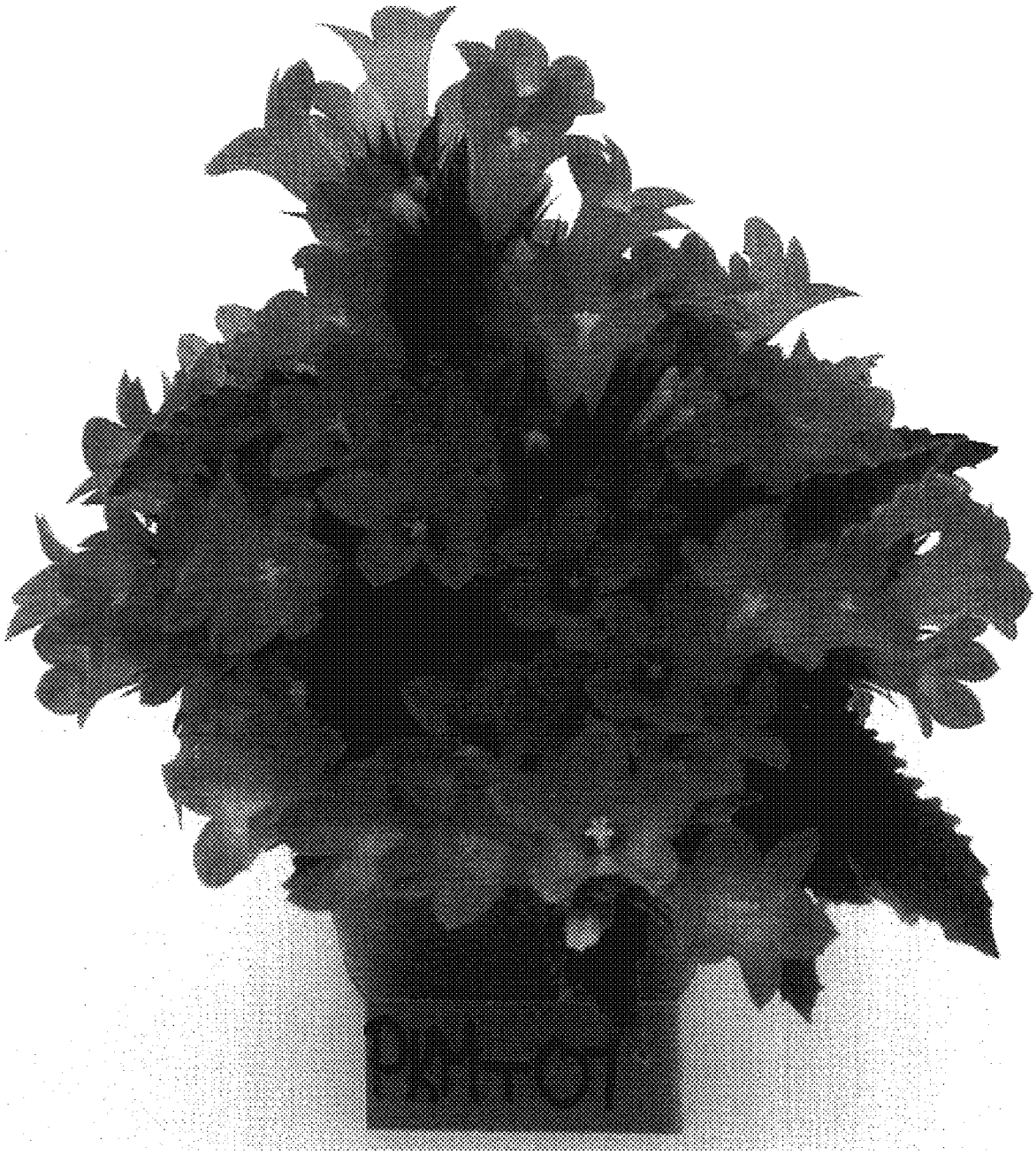
FIG. 1 shows a side perspective view of a typical flowering plant of 'PKMT01' as grown in a 10.5 cm pot.
Figure 2:
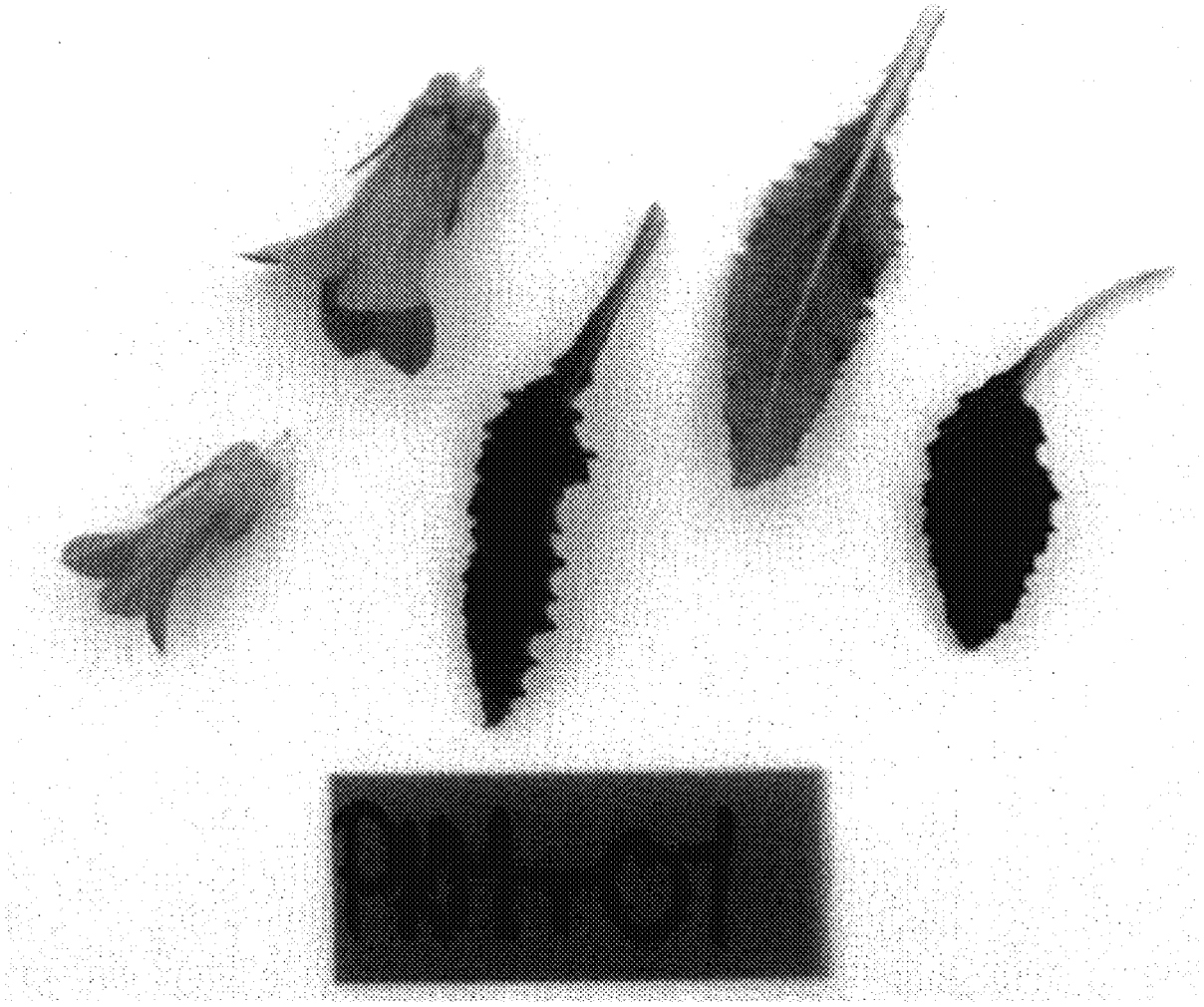
FIG. 2 shows a close-up view of typical flowers and leaves produced by 'PKMT01'.

The new *Campanula* cultivar 'PKMT01' has not been observed under all possible environmental conditions. The phenotype of the new cultivar may vary significantly with variations in environment such as temperature, light intensity, day length, and fertility level without any variance in genotype.

The aforementioned photographs, together with the following observations, measurements and values describe plants of the new *Campanula* cultivar 'PKMT01' as grown in a heated and lighted, glass-covered greenhouse in Søhus, Denmark, under conditions which closely approximate those generally used in commercial practice. Plants of 'PKMT01' are grown in a glass-covered greenhouse where day temperatures in the greenhouse range from 18–20° C. and the night temperatures range from 16–18° C. Ambient light levels used while growing plants of 'PKMT01' are +60 $Wm^2$. Plants of 'PKMT01' are grown with 16 to 18 hour long day photoperiodic treatments. The growth retardant used is 1 Bonzi.

The age of the 'PKMT01' plants described is 18 weeks old (after cutting, but not retarded) and grown in 10.5 cm pots. The photographs and descriptions were taken during the winter season when day temperatures in the glass-covered greenhouse range from 18–20° C. and when night average temperature in the glass-covered greenhouse range from 16–18° C.

Color references are made to The Royal Horticultural Society Colour Chart (R.H.S.), $4^{th}$ ed., except where general colors of ordinary significance are used.

Classification:

*Botanical.*—*Campanula tubulosa.*

*Parentage.*—Selection from *Campanula tubulosa Engl.* wild type plants.

Propagation:

*Type cutting.*—Terminal vegetative cuttings.

*Time to initiate roots.*—About 12 to 15 days at 18 to 21° C. in tunnels in a greenhouse.

*Root description.*—Fine, well branched.

Plant description:

*Form.*—Biennial, herbaceous rosette plant with upright, compact plant habit. Produced in a potted plant. Campanulate flowers in racemes. Freely branching with lateral branches forming at every node.

*Crop time.*—After rooting, about 18 weeks are required to produce finished flowering plants in 10.5 cm pots.

*Plant height* (*soil level to top of plant plane*).—About 15 cm.

*Plant spread* (*width*).—About 20 cm.

*Lateral branches.*—Quantity: About 25 per plant. Length: 3–4 cm. Diameter: 5 mm. 8 leaves per lateral branch.

*Internode length.*—8–9 mm.

*Stem.*—Shape: Round. Strength: Strong. Aspect: Upright and spreading. Pubescence: Hirsute. Color: RHS 138A, green.

*Vigor.*—Vigorous growth rate.

*Foliage description.*—Alternate, single, costate venation. Basal leaves: Length: 3–10 cm. Width: 15–20 mm. Shape: Gladiate. Apex: Acute. Base: Cuneate. Margin: Dentate. Texture: Rough, hirsute (both surfaces). Upper leaves: Length: 22 mm. Width: 7 mm. Shape: Lanceolate, sessile. Margin: Dentate. Texture: Hispid. Color: (young foliage) upperside RHS 139A, green and underside RHS 139C, green; (mature foliage) upperside RHS 136A, green and underside RHS 139B, green.

*Venation.*—Color: upperside RHS 139A, green and underside RHS 139B, green. Pattern: Costate.

*Petiole.*—Length: Up to 35 mm. Diameter: 3×2 mm, flat winged. Texture: Pubescent (both surfaces). Color: RHS 136A, green.

Flower description:

*Flower number per plant.*—About 300–400.

*Flower arrangement and shape.*—Single, upright to outward, large acropetal, campanulate flowers in compressed racemes with large double calyx.

*Natural flowering season.*—Continuous throughout the spring and summer. Season can be extended year round by long day treatments.

*Time to flower.*—8 weeks.

*Rate of flowers opening.*—About 30 flowers per week.

*Flower longevity on the plant.*—5–9 days; however, longevity of individual flowers is highly dependent on temperature and light conditions. Flowers persistent.

*Fragrance.*—Yes, fresh, chilly scent.

*Number of flowers per inflorescence.*—6–8.

*Number of flowers per lateral stem.*—6.

*Inflorescence size.*—Height. 5–8 cm. Diameter: 4–6 cm.

*Flowers.*—Aspect. Upright to outward; sessile. Depth (height): 25 mm. Diameter: 25–32 mm. Deltoid, cuspidate petal lobes: about 9 mm long and 9 mm wide. Corolla color: (upper and undersides) RHS 84A, violet. Throat color: RHS 84D, violet with underside RHS 85C, violet.

*Buds.*—Quantity per lateral stem: 6–7. Length: up to 18 mm. Diameter: up to 5 mm. Shape: oblong, star-shaped cross section. Color: RHS 157A, green-white.

*Petals.*—Arrangement: Sympetalous. Appearance: Fragile. Quantity per flower: 5. Length: 8–9 mm. Width: 8–9 mm. Overall shape: Deltoid. Apex: Cuspidate. Base: Fused. Margin: Entire. Texture: Silky. Color (when opening and fully opened): upperside RHS 84A, violet; underside RHS 85C, violet. Fading to RHS N82A, purple-violet.

*Sepals.*—Arrangement: Sympetalous. Appearance: Matte, hirsute. Quantity per flower: 5 lobes, 5 bracts. Length: 11–12 mm. Width: 5 mm. Overall shape: (sepal) mucronulate, (bracts) folded, round, reflexed. Apex: Mucronulate. Base: Fused. Margin: Entire. Color: (immature) upperside RHS 139C to RHS 139D, green, underside RHS 139D, green. Color: (mature) upperside RHS 139B, green and underside RHS 139C, green.

*Calyx.*—Double with pointed tips (mucronulate), reflexed bracts. *Color: RHS* 139B–C–D, green.

*Peduncles.*—Length: About 5–6 mm. Diameter: 2 mm. Strength: Strong. Angle: varies. Color: 138C, green.

Reproductive organs:

*Androecium.*—Stamen: Quantity: 5, linear anthers initially fused. Anther: Shape: Lanceolate. Length: 4–6 mm. Color: RHS 158B, yellow-white. Pollen: Amount: Good production, plenty. Color: RHS 158B, yellow-white.

*Gynoecium.*—Pistil: Quantity: 1. Length: About 10 mm. Stigma: Shape: Conspicuously pentaparite. Color: RHS 1B, green-yellow. Style: Length: 8 mm. Color: RHS 155D, white. Ovary: Color: RHS 155D, white.

*Seeds.*—Quantity: 30 per flower. Length: About 0.5 to 2.0 mm. Diameter: About 0.5 to 1.0 mm. Texture: Smooth and glabrous. Color of mature seed: RHS 173B, greyed-orange. Color of immature seed: RHS 158A, yellow-white.

*Fruit:.*—Type: Capsule. Length: About 4 mm. Diameter: About 5 to 6 mm. *Color: RHS* 199D, grey-brown.

*Growth retardants.*—1 Bonzi (Paclobutrazol).

*Weather tolerance.*—Plants of the new *Campanula* have exhibited good tolerance to drought, rain and wind, with low temperature resistance to 0° C.

Disease/pest resistance: 'PKMT01' is not resistant to any diseases or pests typical to *Campanula* cultivars.

Disease/pest susceptibility: 'PKMT01' is susceptible to *Botrytis.*

I claim:

1. A new and distinct cultivar of *Campanula* plant named 'PKMT01', as illustrated and described herein.

* * * * *